(12) United States Patent
Chiu (10) Patent No.: US 6,761,705 B1
(45) Date of Patent: Jul. 13, 2004

(54) SAFETY SYRINGE DEVICE WITH A NEEDLE BENDING DEVICE

(76) Inventor: Li-Ssu Chiu, No. 53-9, Lane 167, Tsshiou N. Rd., Changhua City, Changhua (TW)

( * ) Notice: Subject to any disclaimer, the term of this patent is extended or adjusted under 35 U.S.C. 154(b) by 0 days.

(21) Appl. No.: 10/413,292

(22) Filed: Apr. 15, 2003

(51) Int. Cl.[7] .............................................. A61M 5/00
(52) U.S. Cl. ....................... 604/110; 604/192; 604/197; 128/919
(58) Field of Search .............................. 604/110, 192, 604/187, 194, 188, 197, 198, 264, 272; 128/919

Primary Examiner—Brian L. Casler
Assistant Examiner—Kathryn L. Thompson
(74) Attorney, Agent, or Firm—Rosenberg, Klein & Lee (57) ABSTRACT

A safety syringe device includes a tube mounted to the first end of the barrel and the needle extends through the tube. A sleeve is slidably mounted to the first end of the barrel and encloses the tube therein. A metal cover is pivotably connected to an edge of the first end of the sleeve and biased to contact the needle assembly when the sleeve is not yet pulled to its operation position. The metal cover is pivoted to seal the first end of the sleeve when the sleeve is pulled to its operation after the syringe process is completed. The needle is bent by the metal cover when pushing the sleeve back toward the barrel.

6 Claims, 9 Drawing Sheets

SAFETY SYRINGE DEVICE WITH A NEEDLE BENDING DEVICE

FIELD OF THE INVENTION

The present invention relates to safety syringe device having a needle bending device which bends the needle after the syringe is used.

BACKGROUND OF THE INVENTION

Figure 1:
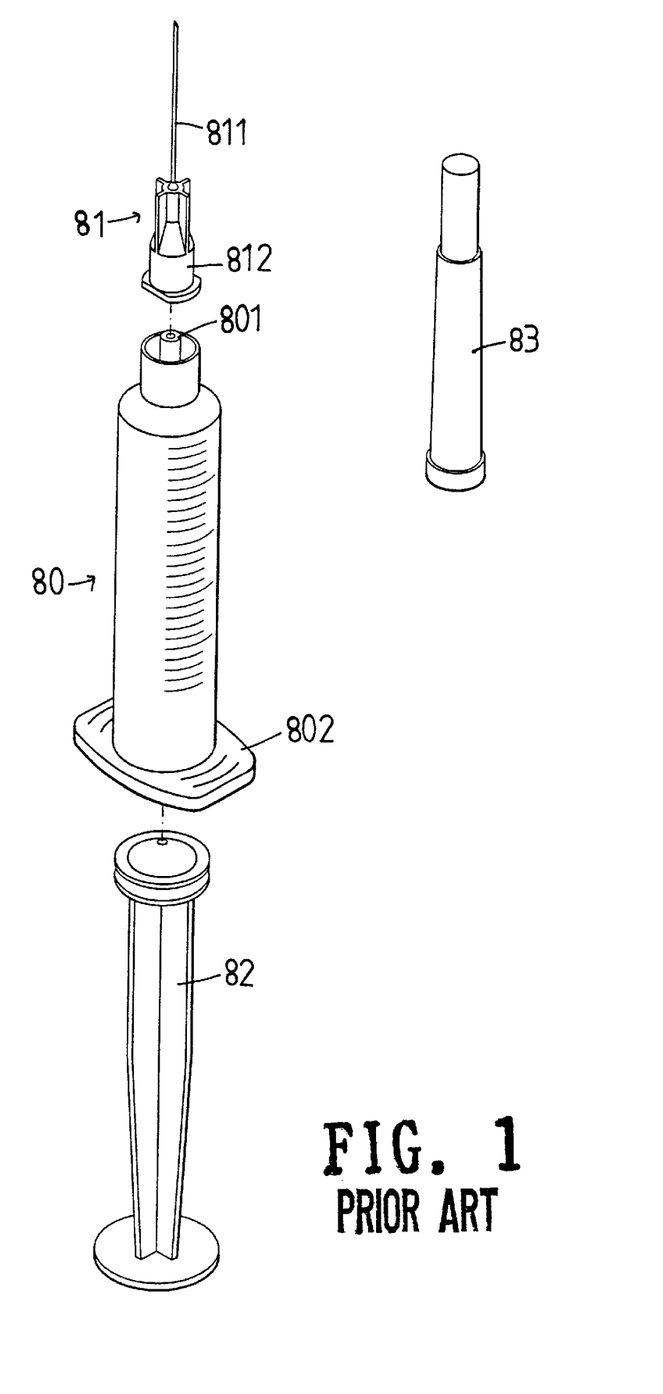
FIG. 1 is an exploded view to show a conventional hypodermic syringe.
Figure 2:
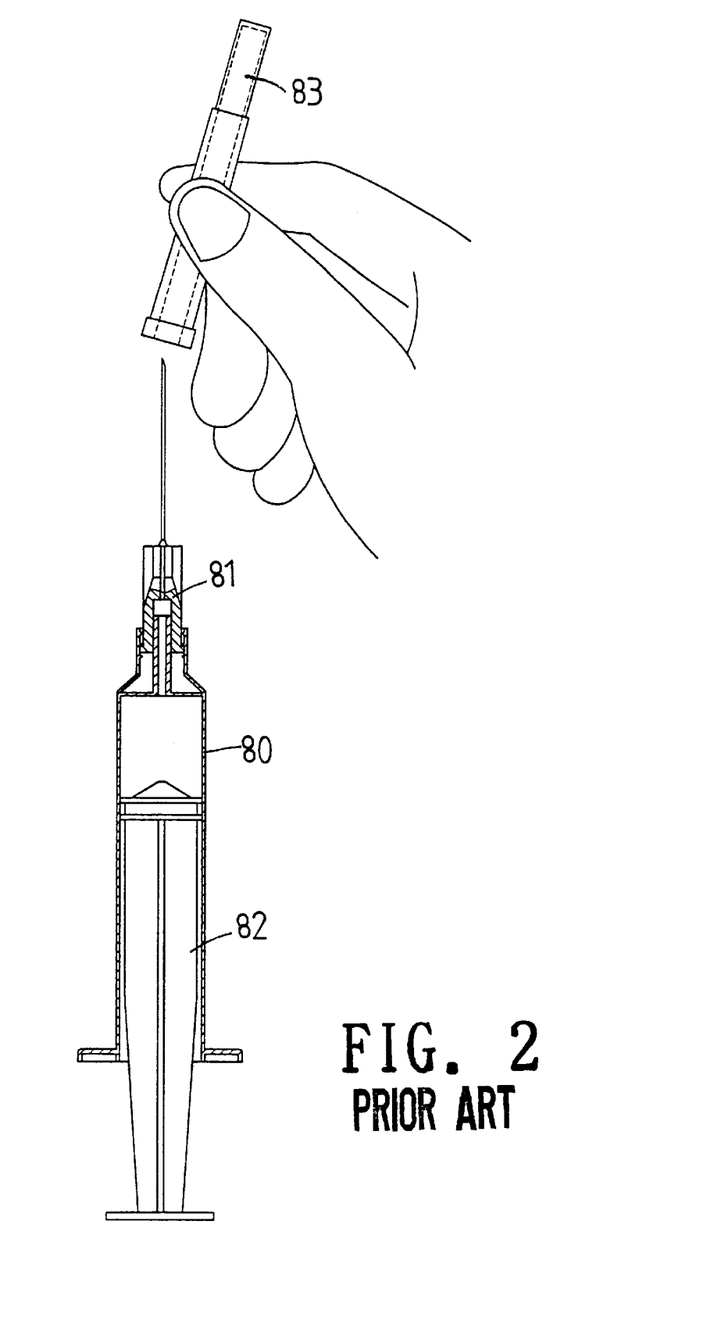
FIG. 2 shows a cap is to be mounted to the needle assembly of the conventional hypodermic syringe.

A conventional hypodermic syringe is disclosed in FIGS. 1 and 2 and generally barrel 80 with a plunger 82 movably received therein. A needle assembly 81 has a locking tip 812 which is secured to the connection port 801 of the barrel 80 and a needle 811 is connected to a needle hub on the locking tip 812. The user may use two fingers to pull the finger flange 802 on the barrel 80 and push the plunger 82 toward the needle 811 to eject the medicine in the barrel 80 from the needle 811. A cap 83 is used to be mounted to the locking tip 812 so as to cover the needle 811 such that the user is not hurt by the needle 811. Nevertheless, the nurses are often hurt by the needles when re-capping the cap 83 and this makes the nurses under a tremendous risk of being affected by various types of diseases. Although there are safety syringe devices developed in the market, a complex mechanism is involved during retrieving the needles into the barrel after the process of injection is completed. In other words, those safety syringe devices are so expensive that only a small part of the hospitals afford then.

The present invention intends to provide a safety syringe device that includes a simple means which bends the needles after the injection is completed.

SUMMARY OF THE INVENTION

In accordance with one aspect of the present invention, there is provided a safety syringe device which comprises a barrel with a plunger movably inserted therein and a needle assembly with a needle is connected to the connection port of the barrel. A tube has a first end and a second end which is fixedly connected to the first end of the barrel and the needle extends through the first end of the tube.

A sleeve is slidably mounted to the barrel and the tube. A cover is pivotably connected an edge of a first end of the sleeve and a part of the cover is biased to be stopped by in contact with the needle assembly when the sleeve is positioned in a ready position. The cover is pivoted to cover the first end of the sleeve when the sleeve is pulled away from the barrel and positioned at an operation position.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 3:
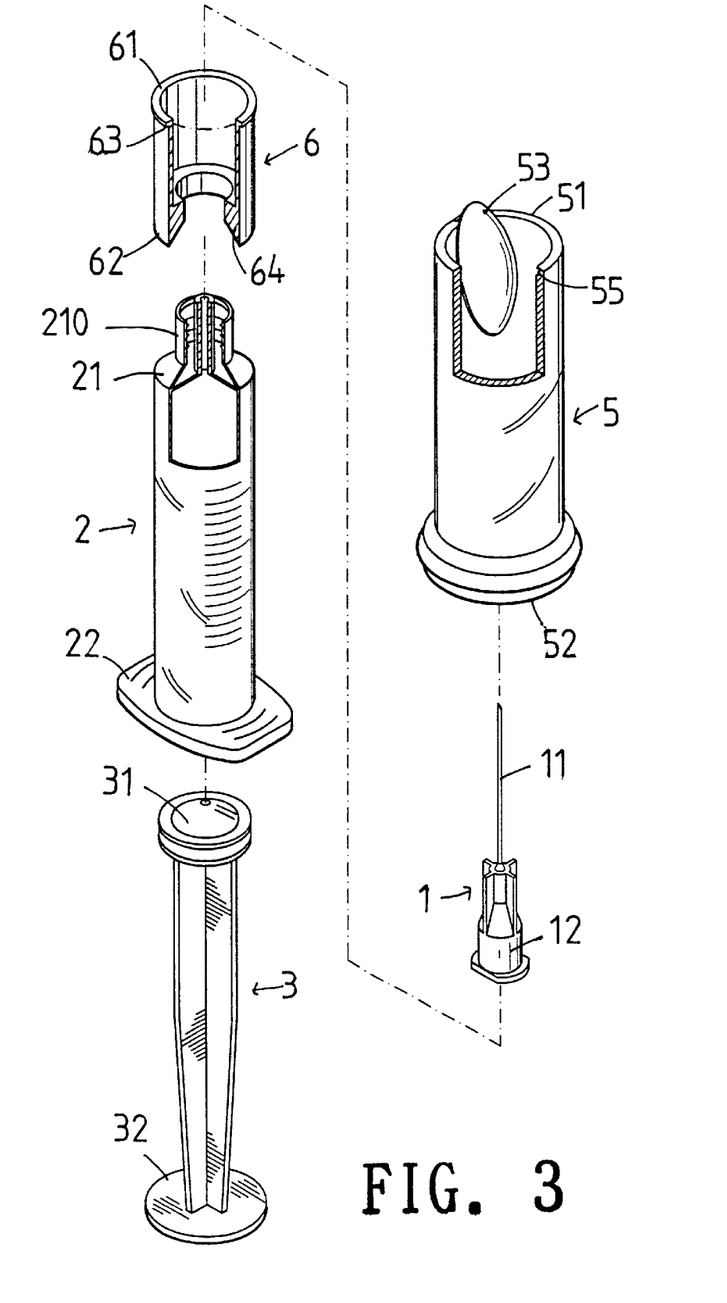
FIG. 3 is an exploded view to show the safety syringe device of the present invention.
Figure 4:
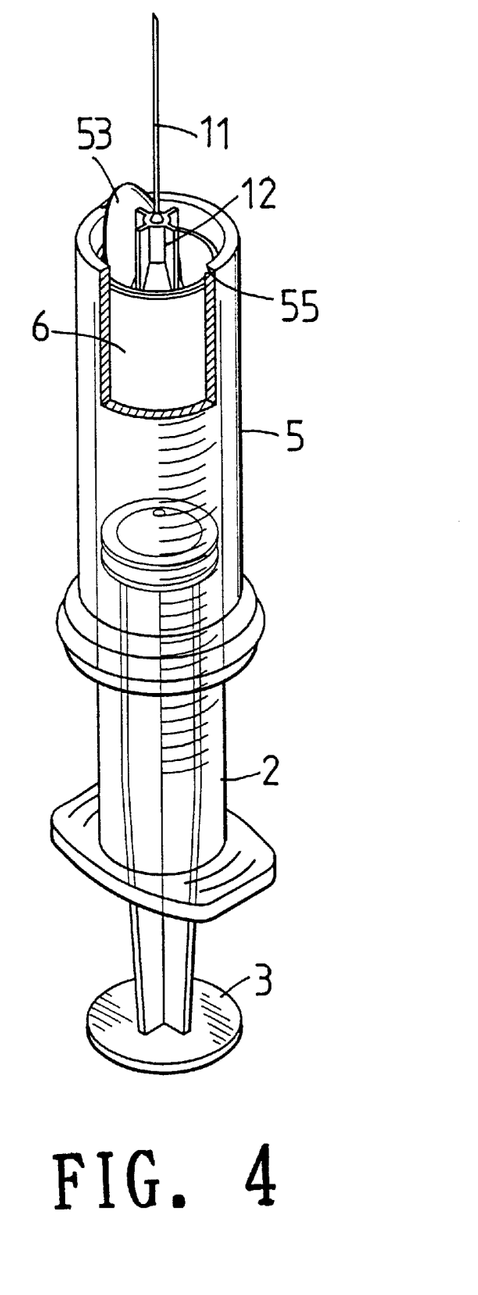
FIG. 4 is a perspective view to show the safety syringe device of the present invention.
Figure 5:
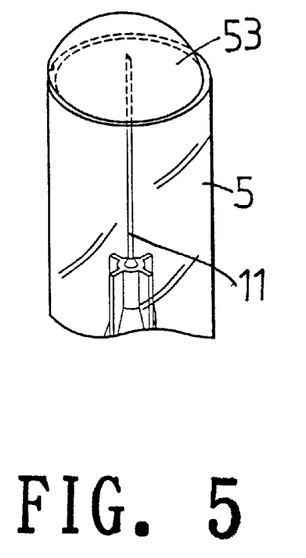
FIG. 5 shows the needle is located beneath the cover when the sleeve is pulled to the operation position.
Figure 6:
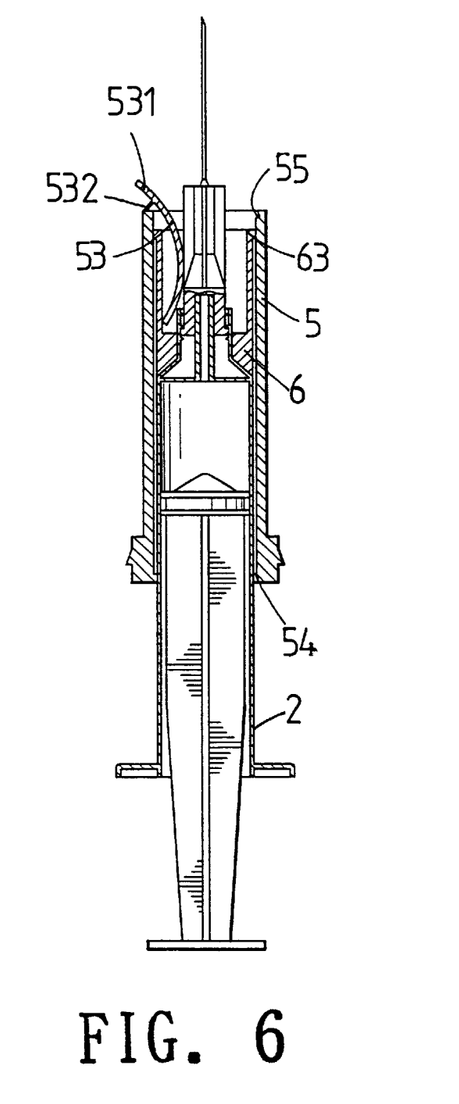
FIG. 6 is a cross sectional view to show the safety syringe device of the present invention when the sleeve is not yet pulled.

Referring to FIGS. 3, 4 and 6, the safety syringe device of the present invention comprises a barrel 2 having a finger flange 22 at a first end thereof and a connection port 210 extending from a second end of the barrel 2. A first inclined end surface 21 is defined in the first end of the barrel 2. A plunger 3 has a stopper 31 at a first end thereof and a thumb rest 32 at a second end of the plunger 3, the stopper 31 is movably received in a passage of the barrel 2. A needle assembly 1 has a locking tip 12 and a needle 11 which extends from the locking tip 12 which is connected to the connection port 210.

A tube 6 has a first end 61 and a second end 62 which has a second inclined end surface 64 so as to be matched with the first inclined end surface 21 of the barrel 2. The tube 6 is fixedly connected to the first end of the barrel 2 and the needle 11 extends through the first end 61 of the tube 6. A positioning flange 63 extends outward from the first end 61 of the tube 6.

Figure 12:
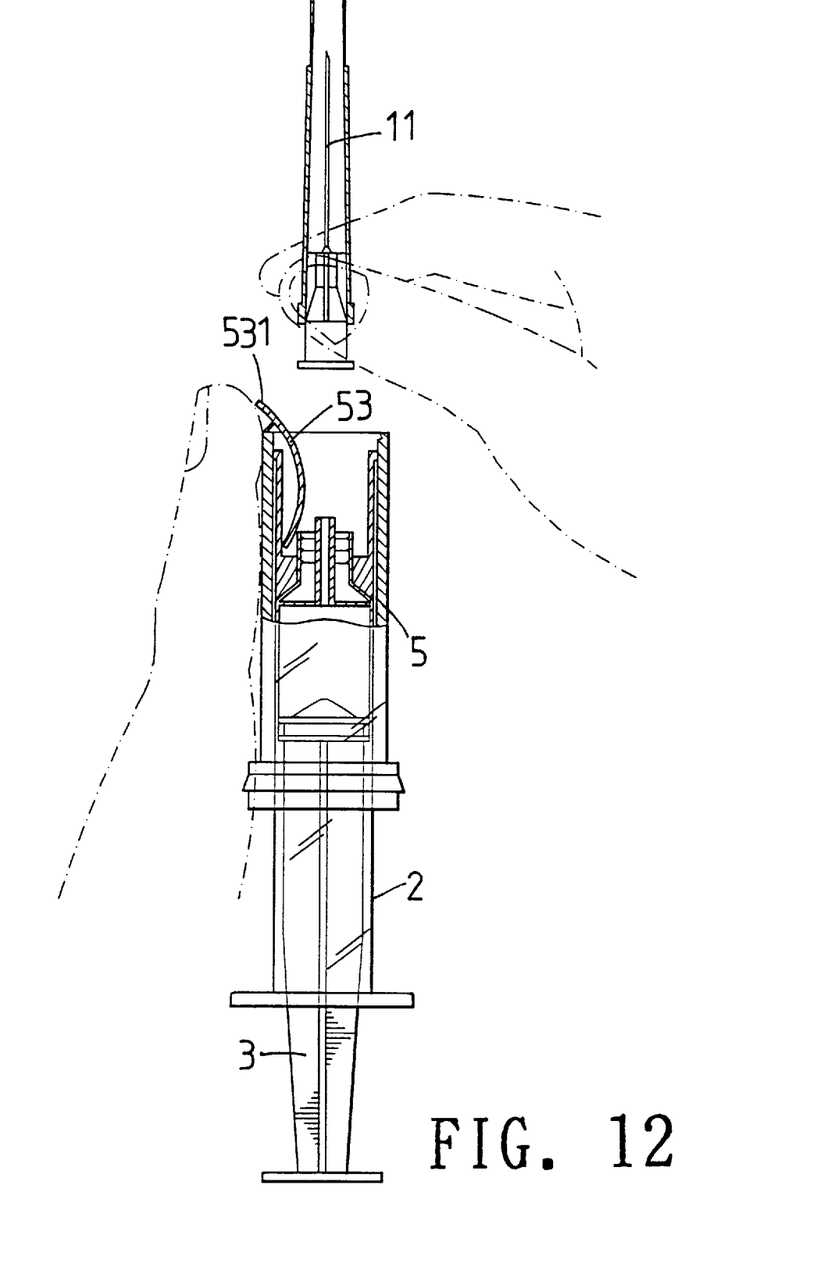
FIG. 12 shows that the needle assembly is to be connected to the connection port of the barrel.

Further referring to FIG. 12, a sleeve 5 is slidably mounted to the barrel 2 and the tube 6. The needle assembly 1 is connected to the connection port 210 of the barrel 2 before it is to be used. A cover 53 made of metal is pivotably connected an edge of a first end 51 of the sleeve 5 at a portion 532 of the cover 53 and an edge 531 of the cover 53 extends out from the first end of the sleeve 5. A part of the cover 53 is biased to contact the needle assembly 1 when the sleeve 5 is positioned in a ready position as shown in FIG. 6. A groove 54 is defined in an inner periphery of the second end of the sleeve 5 and a positioning groove 55 is defined in an inner periphery of the first end of the sleeve 5.

Figure 7:
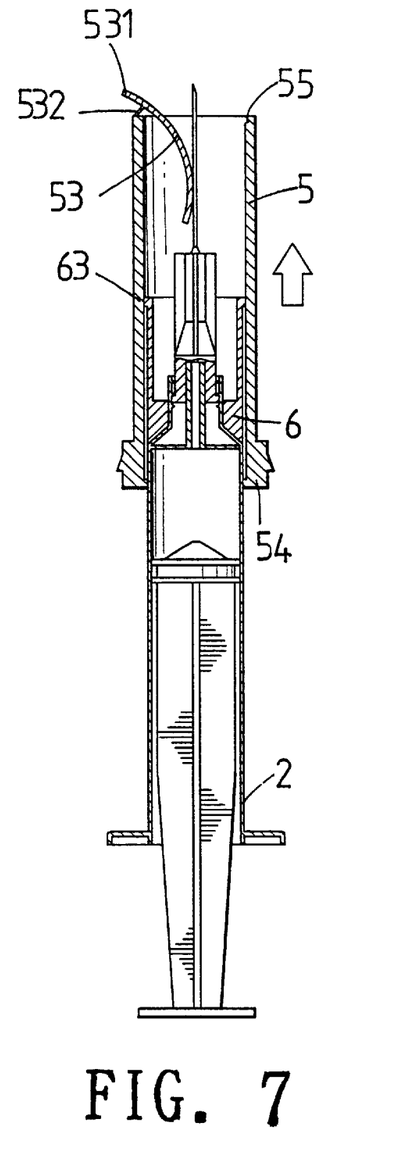
FIG. 7 is a cross sectional view to show the safety syringe device of the present invention when the sleeve is pulling.
Figure 8:
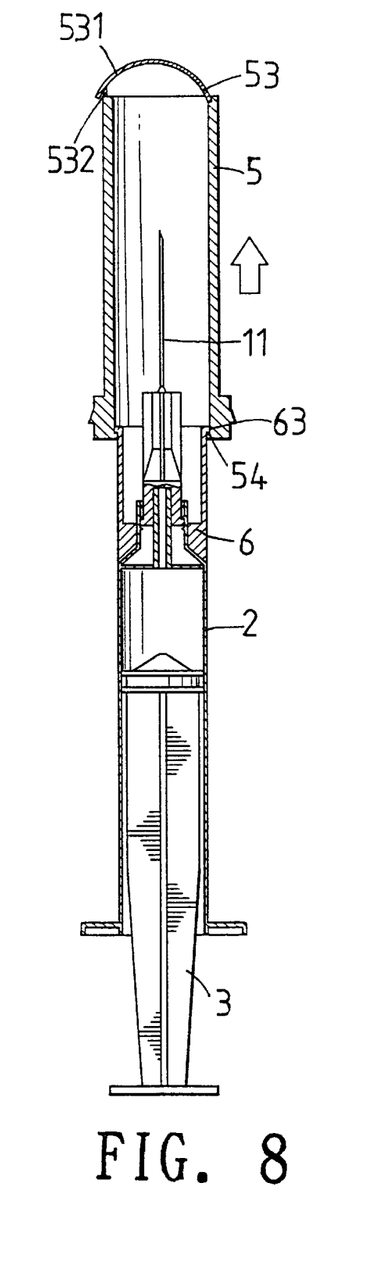
FIG. 8 is a cross sectional view to show the safety syringe device of the present invention when the sleeve is fully pulled.
Figure 9:
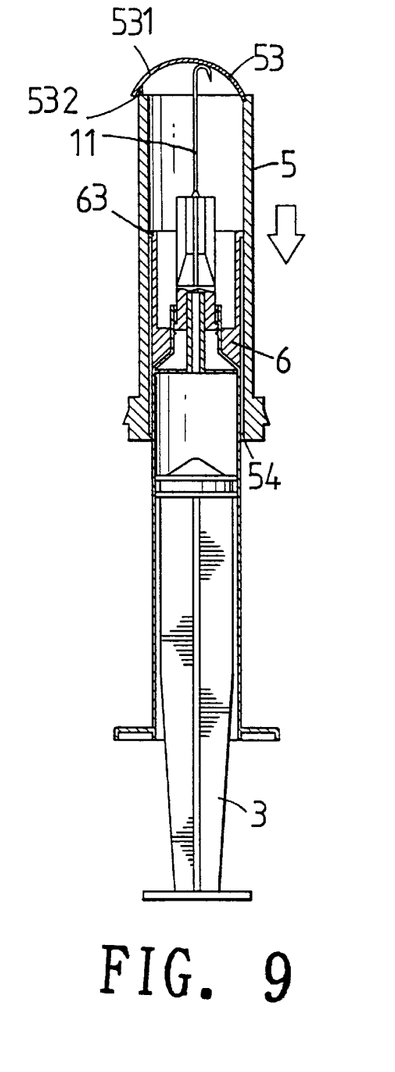
FIG. 9 shows the needle is bent by the cover.

After injection, as shown in FIGS. 7 to 9, the sleeve 5 is pulled in a direction away from the barrel 2 and the cover 53 in the sleeve 5 is pivoted to contact the needle 11 till the sleeve 5 is positioned at its operation position when the positioning flange 63 of the tube 6 is engaged with the groove 54 of the sleeve 5. At the operation position, the cover 53 is completely pivoted and covers the first end of the sleeve 5. The cover 53 is engaged with the positioning groove 55 of the sleeve 5 as shown in FIG. 8. The sleeve 5 is then pushed back till the needle 11 is bent by the cover 53 as shown in FIG. 9.

Figure 10:
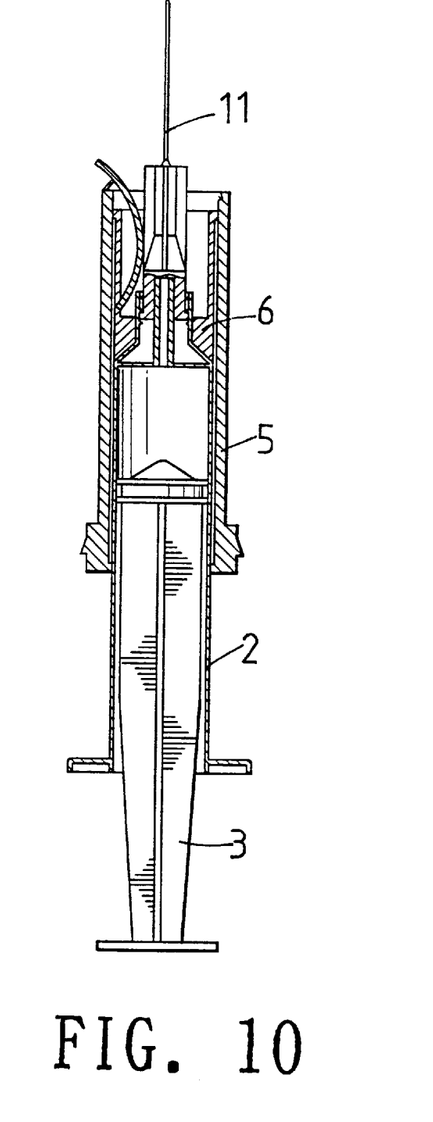
FIG. 10 shows a notch is in the tube to engage the cover.
Figure 11:
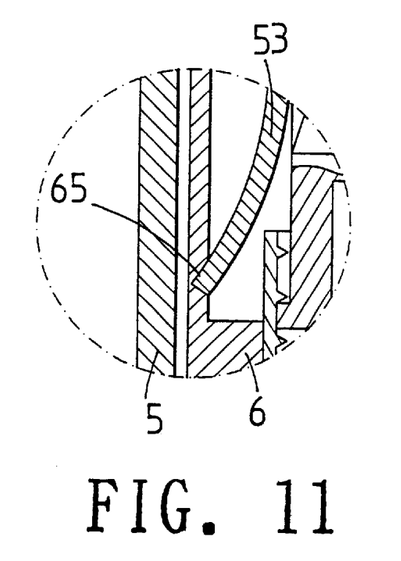
FIG. 11 shows an enlarged view to show the notch engaging the cover.

As shown in FIGS. 10 and 11, a notch 65 may be defined in the inner periphery of the tube 6 and a leading edge of the part of the cover 53 that is located in the tube 6, is engaged with the notch 65 when the sleeve 5 is in ready position.

Figures 13, 14:
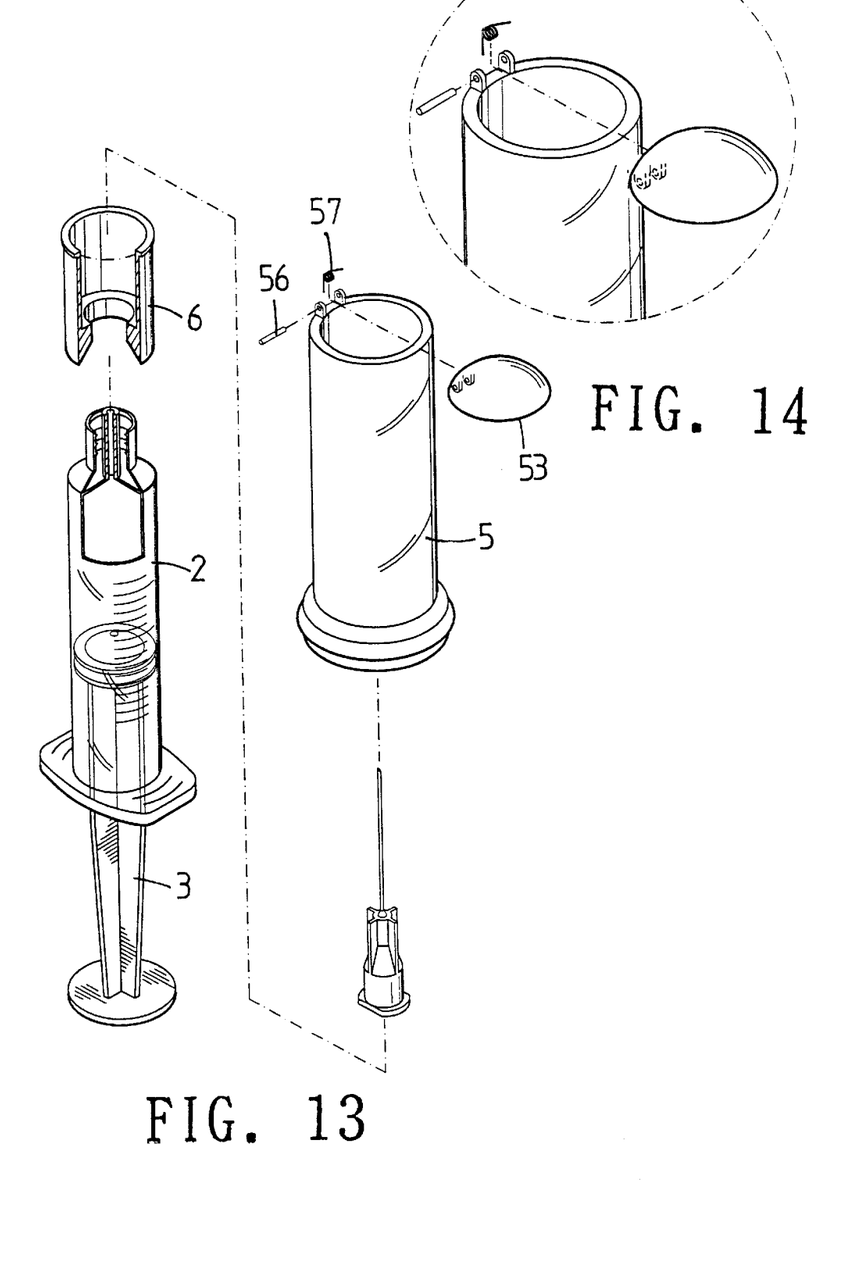
FIG. 13 is an exploded view to show another embodiment of the present invention.
FIG. 14 is an enlarged view to show the cover is connected to the sleeve by lugs and a torsion spring.

FIG. 13 shows that two lugs extend from the edge of the first end of the sleeve 5 and the cover 53 is pivotably connected to the two lugs on the sleeve 5 with a torsion spring 57 connected between the cover 53 and a pin 56 extending through the two lugs.

While we have shown and described the embodiment in accordance with the present invention, it should be clear to those skilled in the art that further embodiments may be made without departing from the scope of the present invention.

What is claimed is:

1. A safety syringe device comprising:

a barrel having a finger flange at a first end thereof and a connection port extending from a second end of the barrel;

a plunger having a stopper at a first end thereof and a thumb rest at a second end of the plunger, the stopper movably received in a passage of the barrel;

a needle assembly having a locking tip and a needle which extends from the locking tip which is connected to the connection port;

a tube having a first end and a second end which is fixedly connected to the first end of the barrel and the needle extending through the first end of the tube, and a sleeve slidably mounted to the barrel and the tube, a cover pivotably connected to an edge of a first end of the sleeve and a part of the cover being biased to contact the needle assembly when the sleeve is positioned in a ready position, the cover being pivoted to cover the first end of the sleeve when the sleeve is pulled in a direction away from the barrel and positioned at an operation position.

2. The safety syringe device as claimed in claim 1, wherein the first end of the barrel includes a first inclined end surface and the second end of the tube has a second inclined end surface which is matched with the first inclined end surface.

3. The safety syringe device as claimed in claim 1, wherein a positioning flange extends outward from the first end of the tube and a groove is defined in an inner periphery of the second end of the sleeve, the positioning flange engaged with the groove when the sleeve is positioned at the operation position.

4. The safety syringe device as claimed in claim 1, wherein a positioning groove is defined in an inner periphery of the first end of the sleeve so that the cover is stopped by and engaged with the positioning groove when the cover covers the first end of the sleeve.

5. The safety syringe device as claimed in claim 1, wherein a notch is defined in an inner periphery of the tube and a leading edge of the cover is engaged with the notch when the sleeve is in ready position.

6. The safety syringe device as claimed in claim 1, wherein two lugs extend from the edge of the first end of the sleeve and the cover is pivotably connected to the two lugs on the sleeve with a torsion spring connected between the cover and a pin extending through the two lugs.

* * * * *